United States Patent
Bates et al.

(10) Patent No.: US 10,569,018 B2
(45) Date of Patent: Feb. 25, 2020

(54) VIAL DOSING SYSTEMS AND METHODS

(71) Applicant: Becton, Dickinson and Company, Franklin Lakes, NJ (US)

(72) Inventors: James Bates, Sparta, NJ (US); Doug Lawrence, Framingham, MA (US); Edward Rosen, Morristown, NJ (US); Robert Banik, Edgewater, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 14/390,974

(22) PCT Filed: Apr. 8, 2013

(86) PCT No.: PCT/US2013/035666
§ 371 (c)(1),
(2) Date: Oct. 6, 2014

(87) PCT Pub. No.: WO2013/155012
PCT Pub. Date: Oct. 17, 2013

(65) Prior Publication Data
US 2015/0065991 A1    Mar. 5, 2015

Related U.S. Application Data

(60) Provisional application No. 61/686,610, filed on Apr. 9, 2012.

(51) Int. Cl.
*A61M 5/20*   (2006.01)
*A61M 5/24*   (2006.01)
(Continued)

(52) U.S. Cl.
CPC ............ *A61M 5/20* (2013.01); *A61M 5/2466* (2013.01); *A61M 5/288* (2013.01); *A61M 5/14593* (2013.01); *A61M 2005/2474* (2013.01)

(58) Field of Classification Search
CPC ........ A61J 1/1412; A61J 1/1418; A61J 1/201; A61J 1/2096; A61M 2005/3128; A61M 5/204; A61M 5/1782
See application file for complete search history.

(56) References Cited

U.S. PATENT DOCUMENTS

| 984,037 A | * | 2/1911 | Sheets | ............... A61M 5/31511 604/125 |
| 1,367,008 A | * | 2/1921 | Bessese | ............... A61M 5/204 604/184 |

(Continued)

FOREIGN PATENT DOCUMENTS

| EP | 0937471 B1 | 9/2005 |
| JP | 2002-525247 A | 8/2002 |

(Continued)

*Primary Examiner* — Scott J Medway
(74) *Attorney, Agent, or Firm* — Dickinson Wright PLLC

(57) ABSTRACT

Vial dosing systems and methods are disclosed. A vial dosing device includes a connecting body coupleable to a vial, a cannulated plunger having a proximal end coupled to the connecting body, a dose chamber adapted to slidably receive a distal end of the cannulated plunger and to expel medicament through a distal end of the dose chamber, and a plunger tip check valve coupled to the cannulated plunger and adapted for fluid flow from the cannulated plunger through the plunger tip check valve into the dose chamber.

28 Claims, 10 Drawing Sheets

(51) Int. Cl.
*A61M 5/28* (2006.01)
*A61M 5/145* (2006.01)

(56) References Cited

U.S. PATENT DOCUMENTS

| | | | | |
|---|---|---|---|---|
| 1,707,880 | A * | 4/1929 | Sheets | A61M 5/315 604/125 |
| 2,607,344 | A * | 8/1952 | Brown | A61M 5/2448 604/125 |
| 3,511,239 | A * | 5/1970 | Tuschhoff | A61M 5/284 604/242 |
| 3,557,787 | A * | 1/1971 | Cohen | A61M 5/31596 604/90 |
| 3,561,596 | A * | 2/1971 | Knox | 206/229 |
| 3,678,931 | A * | 7/1972 | Cohen | A61M 5/284 604/201 |
| 3,807,467 | A * | 4/1974 | Tascher | A61J 1/2096 141/375 |
| 4,153,186 | A * | 5/1979 | Nye | A61M 5/00 137/853 |
| 4,685,596 | A * | 8/1987 | Mattheis | A61C 19/06 222/389 |
| 4,697,622 | A * | 10/1987 | Swift | A61M 5/14276 141/1 |
| 4,986,820 | A * | 1/1991 | Fischer | A61M 5/31513 604/218 |
| 5,067,948 | A | 11/1991 | Haber et al. | |
| 5,181,909 | A * | 1/1993 | McFarlane | A61M 5/315 604/191 |
| 5,334,162 | A * | 8/1994 | Harris | 604/232 |
| 5,393,497 | A * | 2/1995 | Haber et al. | 422/554 |
| 5,413,255 | A * | 5/1995 | Dent | A61D 7/00 222/309 |
| 5,876,372 | A * | 3/1999 | Grabenkort | A61M 5/31596 604/89 |
| 6,003,566 | A | 12/1999 | Thibault et al. | |
| 6,221,053 | B1 | 4/2001 | Walters et al. | |
| 7,452,344 | B2 * | 11/2008 | Jorgensen | A61M 1/029 604/218 |
| 7,731,678 | B2 * | 6/2010 | Tennican | A61J 1/2096 206/363 |
| 8,137,307 | B2 | 3/2012 | Tennican et al. | |
| 2001/0029360 | A1 * | 10/2001 | Miyoshi | A61J 1/2096 604/411 |
| 2002/0107481 | A1 | 8/2002 | Reilly et al. | |
| 2006/0079834 | A1 | 4/2006 | Tennican et al. | |
| 2006/0178631 | A1 * | 8/2006 | Gillespie et al. | 604/139 |
| 2007/0123829 | A1 * | 5/2007 | Atterbury et al. | 604/207 |
| 2010/0286613 | A1 | 11/2010 | Ring | |
| 2010/0312046 | A1 | 12/2010 | Lau et al. | |
| 2011/0184348 | A1 | 7/2011 | Bates et al. | |
| 2011/0230834 | A1 * | 9/2011 | Kavazov | A61J 1/2096 604/140 |

FOREIGN PATENT DOCUMENTS

| | | |
|---|---|---|
| JP | 2008-515594 A | 5/2008 |
| WO | 2003072162 A2 | 9/2003 |
| WO | WO-2010053570 A1 | 5/2010 |
| WO | WO-2011095478 A1 | 8/2011 |
| WO | WO-2012008285 A1 | 1/2012 |

* cited by examiner

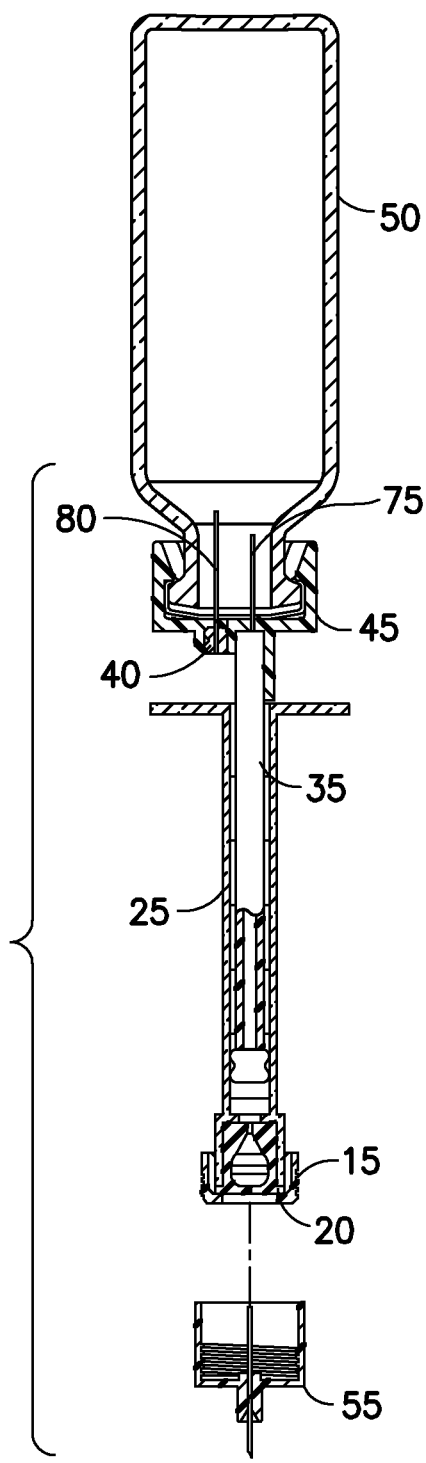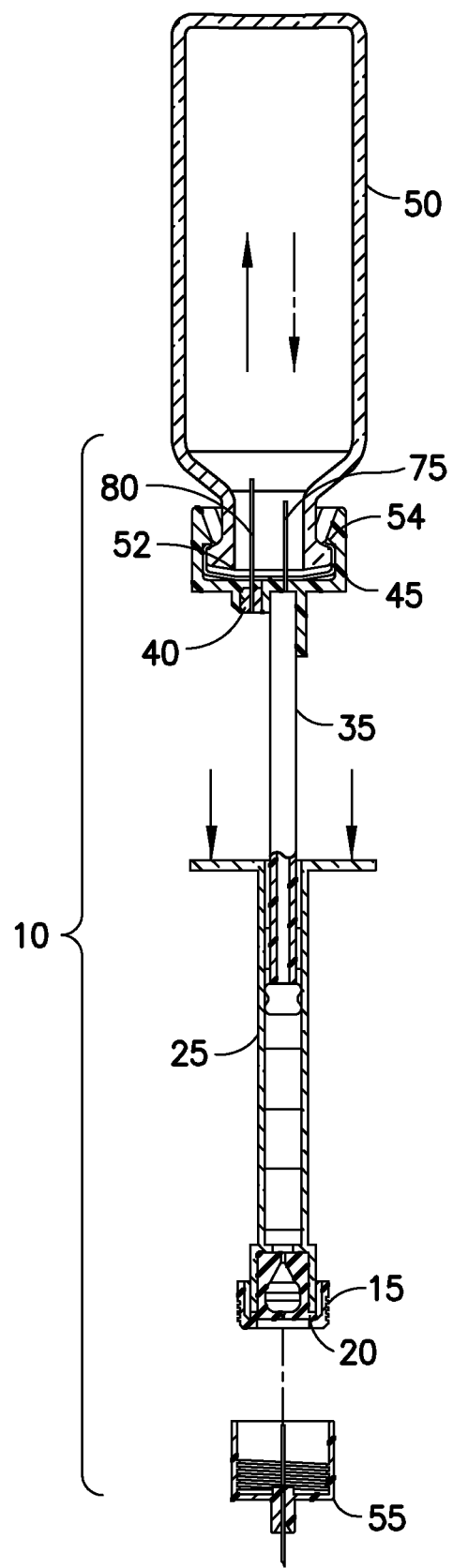
FIG.2A
FIG.2B

VIAL DOSING SYSTEMS AND METHODS

CROSS-REFERENCE TO RELATED APPLICATION

This application claims the benefit of U.S. Provisional Patent Application No. 61/686,610, filed Apr. 9, 2012 in the U.S. Patent and Trademark Office, the disclosure of which is incorporated herein by reference in its entirety.

FIELD OF THE INVENTION

The present invention relates generally to vial dosing systems and methods. More particularly, the present invention relates to a vial dosing device that attaches to a vial to withdraw medicament directly from the vial.

BACKGROUND OF THE INVENTION

In certain circumstances, it is desirable to inject medication directly into human tissue. In the contemporary art, a user draws liquid medicament from a vial using a syringe needle and then injects the medicament into a tissue layer using the same syringe needle.

The contemporary art, however, requires that the user have access to a vial and a separate syringe each time an injection is necessary. Accordingly, the user must carry the vial and one or more syringes on his or her person at all times.

Moreover, the user must repeat the tiresome process of drawing the desired medicament dose from the vial with a syringe needle and then injecting the medicament into a tissue layer using the syringe needle each time an injection is required. If, instead of using a new syringe needle for each injection, the user repeatedly pierces the septum of a vial using the same syringe needle, the syringe needle can dull quickly.

Additionally, contemporary medical vials generally provide unobstructed access to any syringe for the withdrawal of medicament. Often, drugs are offered in multiple concentrations in different medical vials. Medical delivery problems can arise when a syringe with scale markings designed for a higher concentration of a particular drug is inadvertently used to withdraw a lower concentration version of the drug from the vial, or vice versa. More specifically, this can lead to an improper dosage being administered to the patient.

Accordingly, there is a need for a vial dosing device that is fixedly attached to a vial. Such a device can eliminate the need for a user to carry a separate syringe, and can also safeguard against using a vial with a particular concentration of medicament in combination with an improperly marked syringe.

Moreover, there exists a need for a vial dosing device that incorporates disposable injection needles with optimal sharpness and length, to promote less painful injections.

Similarly, there exists a need for a vial dosing device that is less bulky to transport, and can be produced at a lower cost than separate syringes.

SUMMARY OF THE INVENTION

An aspect of embodiments of the present invention is to substantially address the above and other concerns, and provide a vial dosing device that is fixedly attached to a vial to eliminate the need for a user to carry a separate syringe and safeguard against improper connections between a syringe and unobstructed vials.

Another aspect of embodiments of the present invention is to provide a vial dosing device that incorporates disposable injection needles with optimal sharpness and length to promote a less painful injection.

Another aspect of embodiments of the present invention is to provide a vial dosing device that is less bulky to transport and can be produced at a lower cost than separate syringes.

The foregoing and/or other aspects of the present invention are achieved by providing a vial dosing device, including a connecting body couplable to a vial, a cannulated plunger having a proximal end coupled to the connecting body, a dose chamber adapted to slidably receive a distal end of the cannulated plunger and to expel medicament through a distal end of the dose chamber, and a plunger tip check valve coupled to the cannulated plunger and adapted for fluid flow from the cannulated plunger through the plunger tip check valve into the dose chamber.

The foregoing and/or other aspects of the present invention are also achieved by providing a combination, including a vial dosing device and a vial. The vial dosing device includes a connecting body coupled to the vial, a cannulated plunger having a proximal end coupled to the connecting body, a dose chamber adapted to slidably receive a distal end of the cannulated plunger and to expel medicament through a distal end of the dose chamber, and a plunger tip check valve coupled to the cannulated plunger and adapted for fluid flow from the cannulated plunger through the plunger tip check valve into the dose chamber. The cannulated plunger is substantially enclosed by the connecting body. The connecting body is at least partially enclosed by the vial.

The foregoing and/or other aspects of the present invention are also achieved by providing a method of using a vial dosing device, including coupling a connecting body to a medical vial containing medicament, and displacing a cannulated plunger proximally with respect to the dose chamber to withdraw a dose of medicament from the medical vial into the dose chamber through a plunger tip check valve coupled to the cannulated plunger. A proximal end of the cannulated plunger is coupled to the connecting body. A distal end of the cannulated plunger is slidably received in the dose chamber.

Additional and/or other aspects and advantages of the present invention will be set forth in the description that follows, or will be apparent from the description, or may be learned by practice of the invention.

BRIEF DESCRIPTION OF THE DRAWINGS

The various objects, advantages and novel features of illustrative embodiments of the present invention will be more readily appreciated from the following detailed description when read in conjunction with the appended drawings, in which:

FIGS. 2A-C illustrate operation of the vial dosing device of FIG. 1;

DETAILED DESCRIPTION OF THE ILLUSTRATIVE EMBODIMENTS

Figure 1:
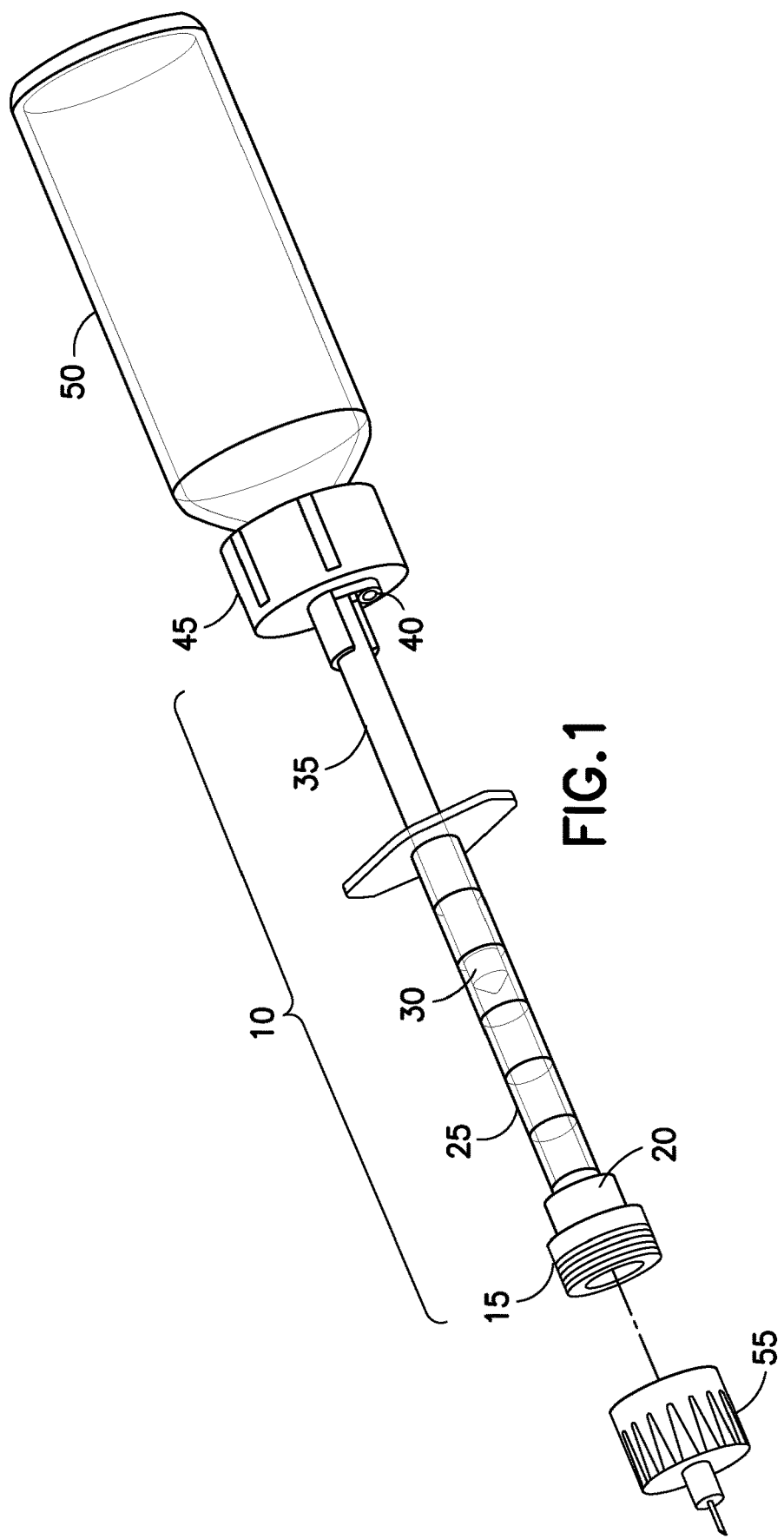
FIG. 1 is a perspective view of a vial dosing device in accordance with an embodiment of the present invention, in combination with a vial and a needle.
Figure 2C:
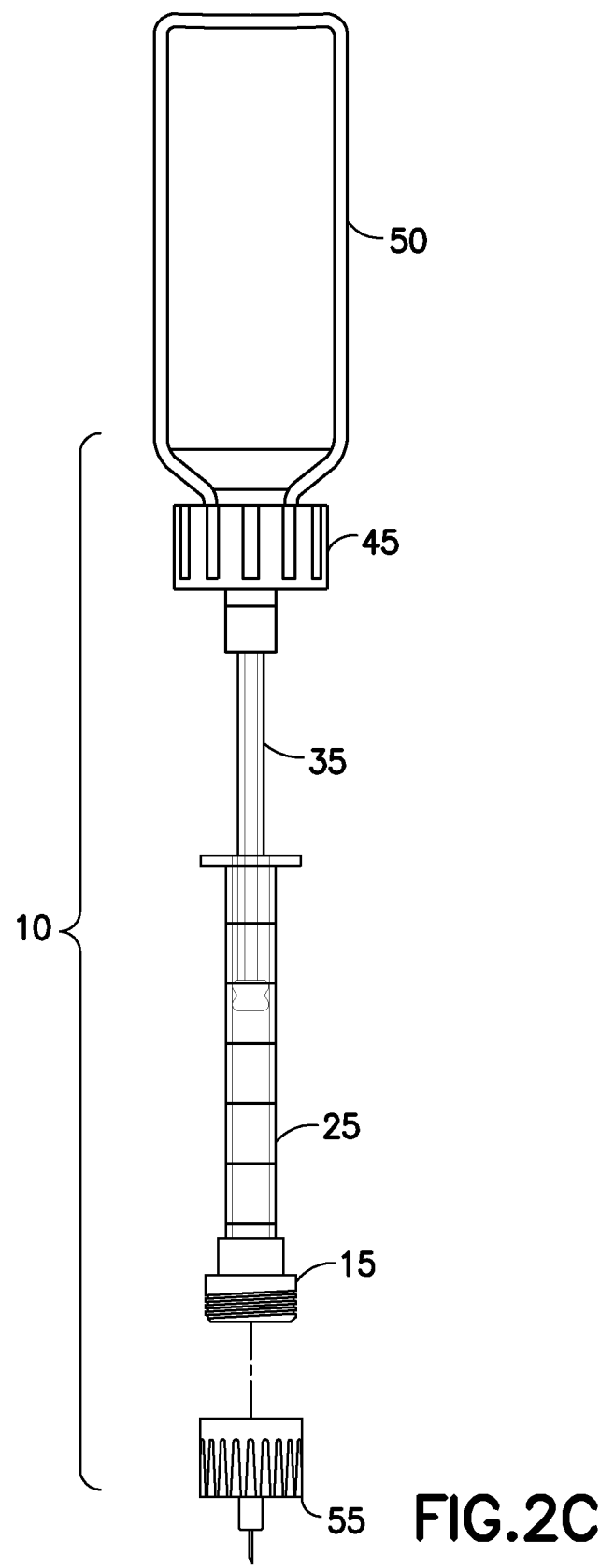

As will be appreciated by one skilled in the art, there are numerous ways of carrying out the examples, improvements, and arrangements of a vial dosing device in accordance with embodiments of the present invention disclosed herein. Although reference will be made to the illustrative embodiments depicted in the drawings and the following descriptions, the embodiments disclosed herein are not meant to be exhaustive of the various alternative designs and embodiments that are encompassed by the disclosed invention.

Although various persons (for example, but not limited to, a patient or a healthcare professional) can operate or use illustrative embodiments of the present invention, for brevity an operator or user will be referred to as a "user" hereinafter.

In illustrative embodiments of the present invention described herein, a "distal" direction refers to a direction toward an injection site, and a "proximal" direction refers to a direction away from an injection site, although such directions are not limiting.

Illustrative embodiments in accordance with the present invention are depicted in FIGS. 1-5. According to one embodiment, a vial dosing device is coupled to a vial and can be used with any needles known in the art, including, but not limited to, a standard disposable injection needle, such as a standard pen needle or a double-ended pen needle. Such needles can inject liquid medicament into a layer of tissue or other injection site. Double-ended pen needles are preferred because they can provide sharper ends and a less painful injection. A vial can be any vial known in the art, including, but not limited to, a medical vial.

FIGS. 1 and 2A-C depict an illustrative embodiment of a vial dosing device 10 in combination with a vial 50 and a needle 55. The vial dosing device 10 includes a needle adapter 15, a dose chamber septum 20, a dose chamber 25, a plunger tip check valve 30, a cannulated plunger 35 on which the plunger tip check valve 30 is disposed, a venting check valve 40, and a connecting body 45. The needle adapter 15 includes any needle adapter known in the art, including, but not limited to, a threaded pen needle adapter. The plunger tip check valve 30 can include any check valve known in the art, including, but not limited to, a low durometer check valve, or a duck-bill shaped check valve. The venting check valve 40 can include any check valve known in the art, including, but not limited to, a press-in check valve. The connecting body 45 can include any connecting body known in the art, including, but not limited to, a snap-connect body adapted to snap over a flange 54 of the vial 50.

As subsequently discussed in greater detail, the connecting body 45 couples to a vial 50. The venting check valve 40 is coupled to the connecting body 45, so that air can flow from outside the vial 50 through the venting check valve 40, through at least a portion of the connecting body 45, and into the vial 50. A proximal end of the cannulated plunger 35 is coupled to the connecting body 45, and is adapted for fluid flow with the vial 50 through the connecting body 45. The dose chamber 25 slidably receives a distal end of the cannulated plunger 35. The dose chamber 25 is further adapted to expel medicament through a distal end of the dose chamber 25. The plunger tip check valve 30 is coupled to the cannulated plunger 35, and is adapted for fluid flow from the cannulated plunger 35, through the plunger tip check valve 30, and into the dose chamber 25. The needle adapter 15 is coupled to the dose chamber 25 and is couplable to the needle 55. Preferably, as shown in FIG. 1, the needle 55 is a double-ended pen needle 55. One skilled in the art will understand, however, that other needles can be employed without departing from the scope of the present invention. The dose chamber septum 20 is disposed at a distal end of the dose chamber 25.

Thus, compared to conventional devices and syringes, an embodiment of the present invention provides a vial dosing device that is less bulky to transport, less costly, and more environmentally friendly to manufacture. For example, keeping large inventories of needles and reusable vial dosing devices can use storage space more efficiently and be more cost effective than keeping large inventories of disposable syringes.

Furthermore, according to one embodiment, the connecting body 45 connects only to specific vials, thereby reducing the likelihood of using an undesired vial. For example, the connecting body 45 can be unable to snap or otherwise couple to an opening of an undesired vial. Such a connecting body 45 can, for example, prevent use of a vial with a medicament concentration that does not correspond to markings of the dose chamber 25.

Preferably, the vial dosing device 10 is initially packaged in a collapsed configuration, as illustrated in FIG. 2A. In this state, the plunger tip check valve 30 is disposed near the distal end of the dose chamber 25, and a majority of the plunger 35 is disposed within the dose chamber 25. According to one embodiment, in this collapsed configuration, the plunger tip check valve 30 rests adjacent to the dose chamber septum 20.

In operation, a user couples the vial dosing device 10 to the vial 50. For example, after a user removes a vial cap from a vial 50 and exposes the vial septum 52, the user couples the vial dosing device 10 to the vial 50 by snapping the connecting body 45 proximally over a flange 54 of the vial 50, to lock the vial dosing device 10 in place on a neck of the vial 50. One skilled in the art will understand that other methods of connecting the vial 50 with the connecting body 45, such as mating or screw threads, can be employed without departing from the scope of the present invention.

The connecting body 45 includes a hollow fluid needle 75 and a hollow venting needle 80. A proximal end of the fluid needle 75 pierces the vial septum 52 to create a liquid fluid passageway from the vial 50 to the plunger 35. A proximal end of the venting needle 80 pierces the vial septum 52 to vent the vial 50. The venting needle 80 is adapted for air flow with the venting check valve 40, which creates an air path through the venting check valve 40, through the venting needle 80, and into the vial 50. According to one embodiment, the air path can include a bacterial filter or a tortuous path to prevent undesired bacteria, viruses and other microorganisms from entering the vial 50 through the vent.

In operation, once the vial dosing device 10 is connected to the vial 50, the user pulls the dose chamber 25 to displace it distally with respect to the cannulated plunger 35 and away from the vial 50, to draw an appropriate dose of medicament or other fluid from the vial 50, as illustrated in FIG. 2B. Although other fluids can be employed, the liquid in the vial 50 will hereinafter be referred to as "medicament." The user withdraws a desired dose of medicament by reading dose measurements, which are represented by scale markings on side walls of the dose chamber 25.

More specifically, when a user pulls the dose chamber 25 to displace it distally with respect to the cannulated plunger 35, away from the vial 50, air is drawn into the vial 50 through the venting check valve 40 and a vacuum can be created in the dose chamber 25 by its relative distal displacement, pulling medicament from the vial through the plunger tip check valve 30 and into the dose chamber 25.

Prior to injecting the withdrawn medicament into a layer of tissue or other injection site, the user couples a conventional hollow-needle pen needle assembly 55 to the vial dosing device 10, for example, by threading the pen needle 55 onto the needle adapter 15 of the vial dosing device 10. The proximal end of the needle 55 pierces the dose chamber septum 20, creating a fluid path for fluid flow from the dose chamber 25 through the needle 55.

According to one embodiment, the user primes the vial dosing device 10 by holding the needle 55 with the connected vial dosing device 10, with the vial 50 preferably oriented upward, and displacing the dose chamber 25 proximally with respect to the cannulated plunger 35 to eject any excess air or adjust the dose of medicament prior to injecting the medicament.

The user injects the withdrawn medicament by piercing a layer of tissue or other injection site with the distal end of the needle 55 and then pressing the vial 50 and/or the plunger 35 distally with respect to the dose chamber 25 and toward the layer of tissue or other injection site to expel the dose of medicament from the dose chamber 25, through the needle 55, and into the layer of tissue or other injection site.

The vial dosing device 10 can remain coupled to the vial 50 for subsequent injections until the medicament within the vial 50 is exhausted.

Figure 3:
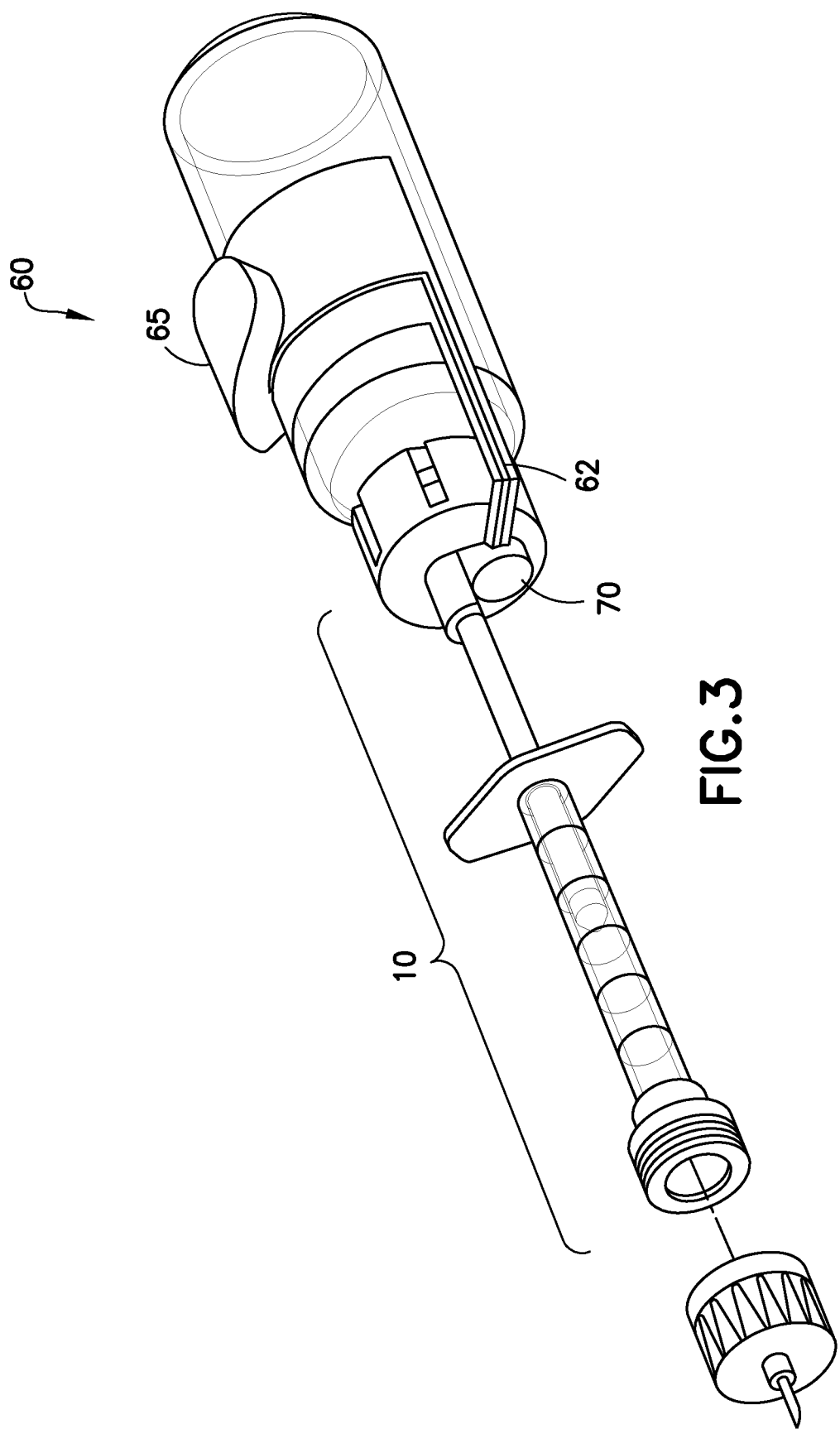
FIG. 3 is a perspective view of the vial dosing device of FIG. 1 and a manual pump in accordance with another embodiment of the present invention, in combination with a vial and a needle.

FIG. 3 illustrates a vial dosing device 10 with a manual pump 60, in combination with a vial and a needle, according to an embodiment of the present invention. Optionally, any pump known in the art can be used in place of the disclosed manual pump.

Figure 4A:
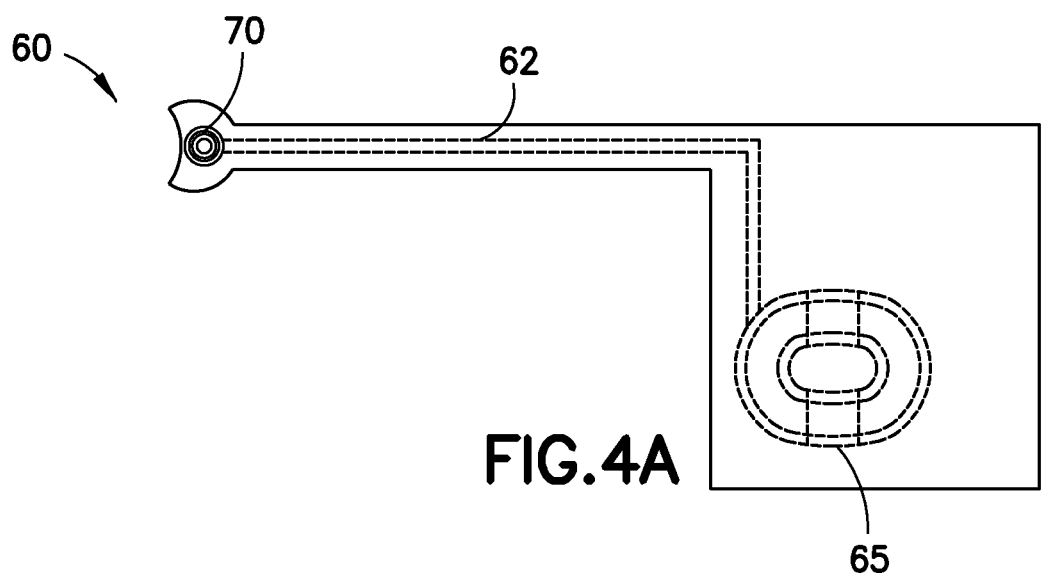
FIGS. 4A-C are views of an illustrative embodiment of a manual pump in accordance with another embodiment of the present invention.
Figure 4B:
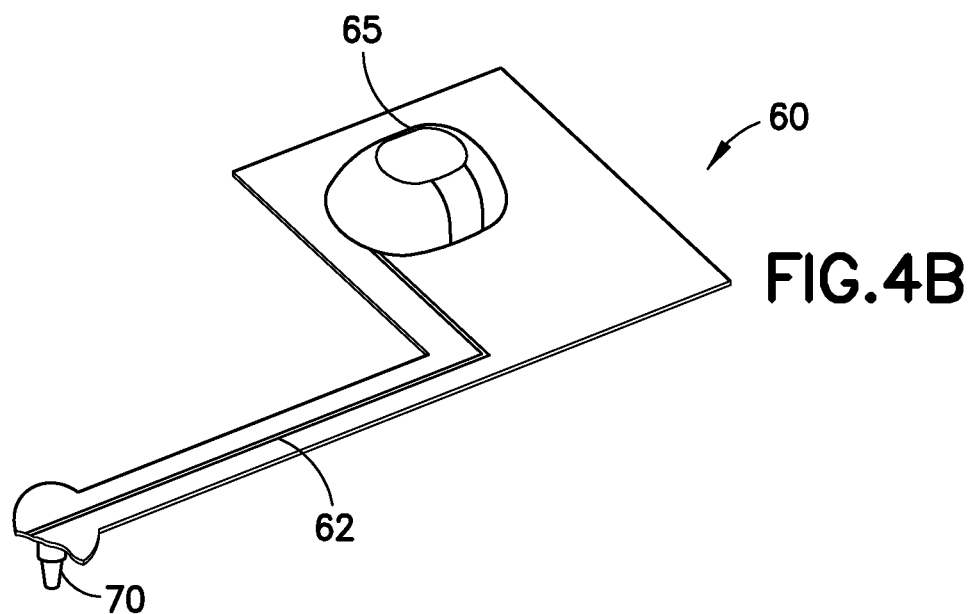
Figure 4C:
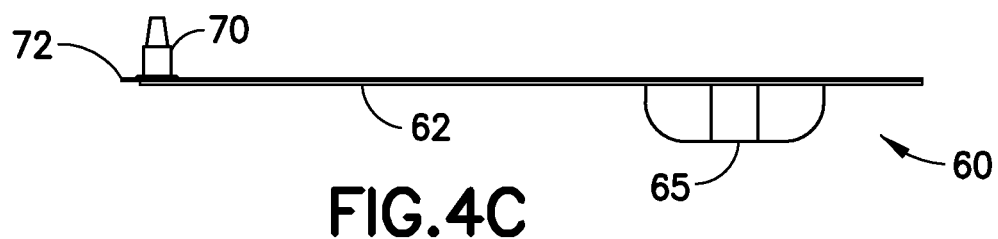

FIGS. 4A-C show a manual pump 60 according to an embodiment of the present invention. Preferably, the manual pump 60 is a thin film manual pump.

The manual pump 60 includes a channel 62, a bladder 65, and a pump check valve 70. The channel 62 can include any channel known in the art, including, but not limited to, a vacuum-formed air channel. The pump check valve 70 can include any check valve known in the art, including, but not limited to, a polyurethane molded duckbill check valve 70. The pump check valve 70 can be coupled to the channel using any coupling mechanism known in the art, including, but not limited to, ultrasonic or radio frequency (RF) welding.

According to one embodiment, the channel 62 is coupled to the bladder 65 and to the pump check valve 70 for air flow from the bladder 65, through the channel 62, and through the pump check valve 70.

Preferably, the bladder is resilient. For example, an open cell foam inside the bladder 65 can act as a return by providing resiliency to the bladder.

The manual pump 60 can be coupled to the vial 50 by any coupling mechanism known in the art, including, but not limited to, a pressure sensitive adhesive 72 to adhere to the vial 50.

The pump check valve 70 of the manual pump 60 can be welded into or otherwise coupled to the venting check valve 40. The manual pump 60 can be adhesively or otherwise coupled to the vial 50. The user can pump air into the vial 50 by pressing the air bladder 65 of the manual pump 60. Manually pumping air into the vial 50 via the manual pump 60 can create a larger pressure differential between the interior of the vial and the atmosphere than other illustrative embodiments in which air is vented into the vial 50 due to a vacuum created during withdrawal of medicament from the vial 50.

FIGS. 5A-F show a submerged vial dosing device 110 in combination with a vial 150 and a hollow-needle pen needle assembly 155, according to an embodiment of the present invention. The submerged vial dosing device 110 includes a needle adapter 115, a dose chamber septum 120, a dose chamber 125, a plunger tip check valve 130, a plunger 135, and a connecting body 145. The needle adapter 115 can include any needle adapter known in the art, including, but not limited to, a threaded pen needle adapter. The plunger tip check valve 130 can include any check valve known in the art, including, but not limited to, a low durometer or duck-bill shaped check valve. The connecting body 145 can include any connecting body known in the art, including, but not limited to, a snap-connect body.

In an illustrative embodiment of the present invention, the connecting body 145 is couplable to the vial 150, and the cannulated plunger 135 is substantially enclosed by the connecting body 145. The cannulated plunger 135 and the connecting body 145 are at least partially enclosed by the vial 150.

Because the vial dosing device 110 is submerged, it is less bulky to transport and less costly and more environmentally friendly to manufacture, compared to conventional devices and syringes. For example, keeping large inventories of needles and reusable vial dosing devices can be more space efficient and more cost effective than keeping large inventories of disposable syringes.

Furthermore, the connecting body 145 can be adapted to connect only to specific vials, thereby reducing the likelihood of using an undesired vial, for example, with a medicament concentration that does not correspond to markings of the dose chamber 125.

A proximal end of the cannulated plunger 135 is coupled to the connecting body 145, and is adapted for fluid flow with the vial 150 through the connecting body 145. The dose chamber 125 slidably receives a distal end of the cannulated plunger 135. The dose chamber 125 is further adapted to expel medicament through a distal end of the dose chamber 125. The plunger tip check valve 130 is coupled to the cannulated plunger 135, and is adapted for fluid flow from the cannulated plunger 135 through the plunger tip check valve 130, and into the dose chamber 125. The needle adapter 115 is coupled to the dose chamber 125 and is couplable to a needle 155, such as a double-ended pen needle. The dose chamber septum 120 is disposed at a distal end of the dose chamber 125.

According to one embodiment, the submerged vial dosing device 110 is positioned into a vial 150 during filling, and can remain coupled to the vial 150 for the duration of the lifespan of the vial 150. The submerged plunger 135 and dose chamber 125 of the vial dosing device 110 preferably incorporate drug-compatible injection molded components, to minimize the number of components and to provide cost-effective product, and electroless nickel plating, to prevent corrosion and wear.

Figure 5A:
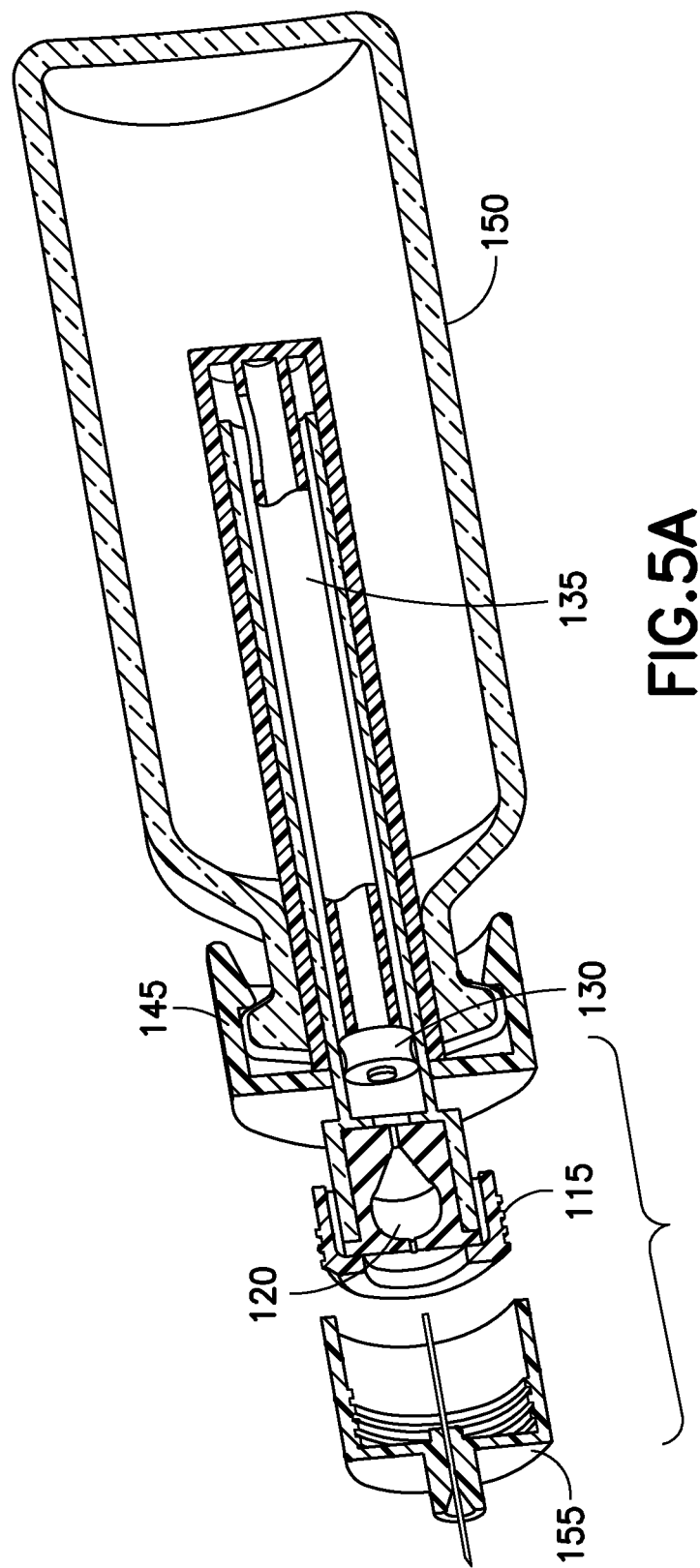
FIGS. 5A-F illustrate a submerged vial dosing device in accordance with another embodiment of the present invention, in combination with a vial and a needle.
Figure 5B:
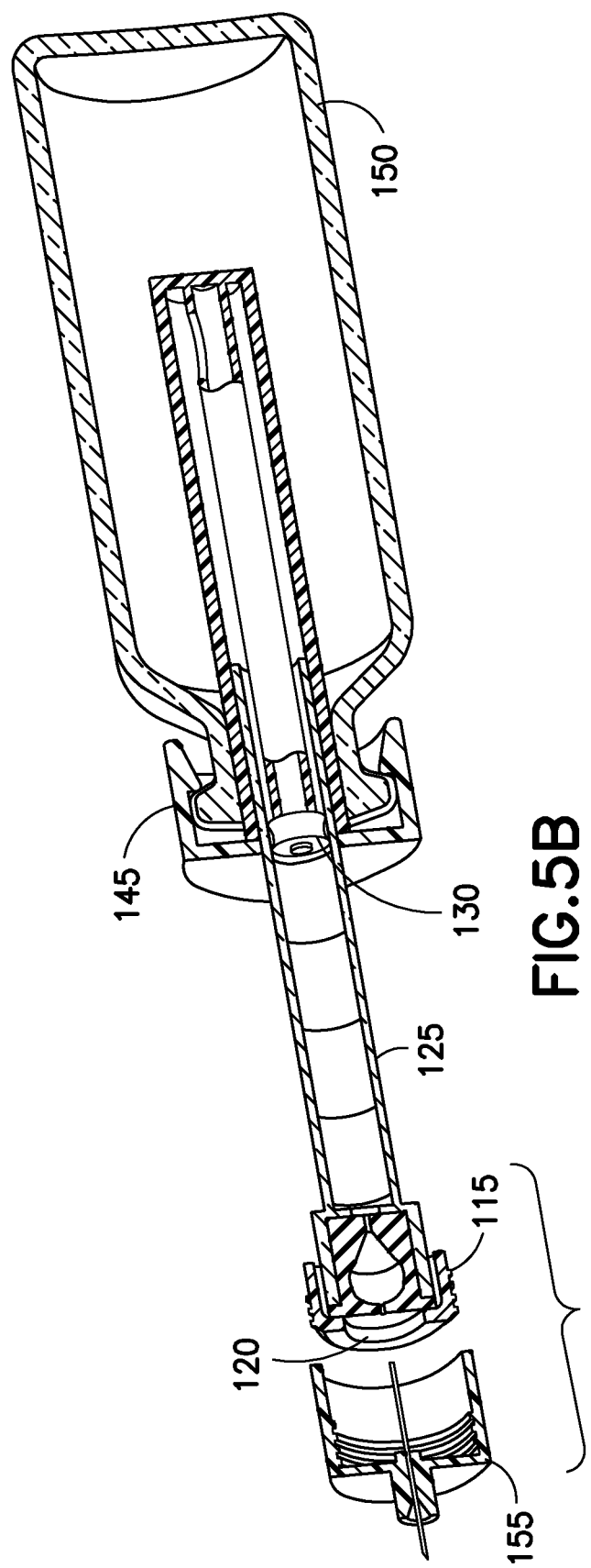
Figure 5C:
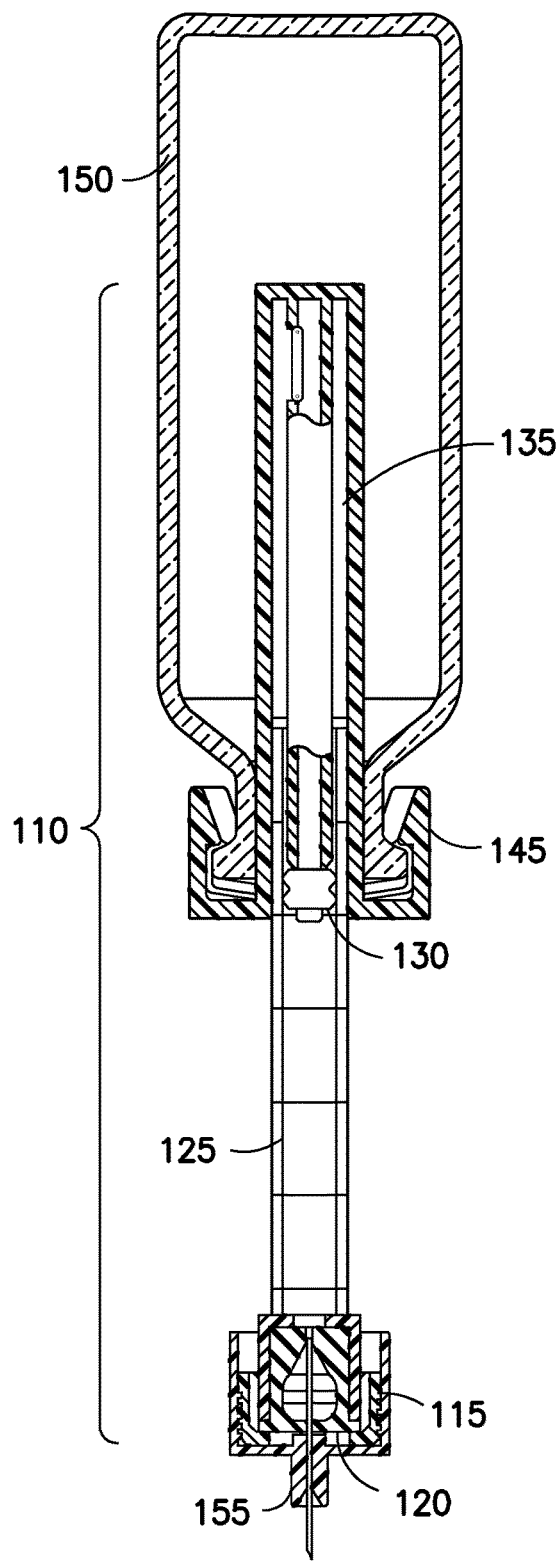
Figure 5D:
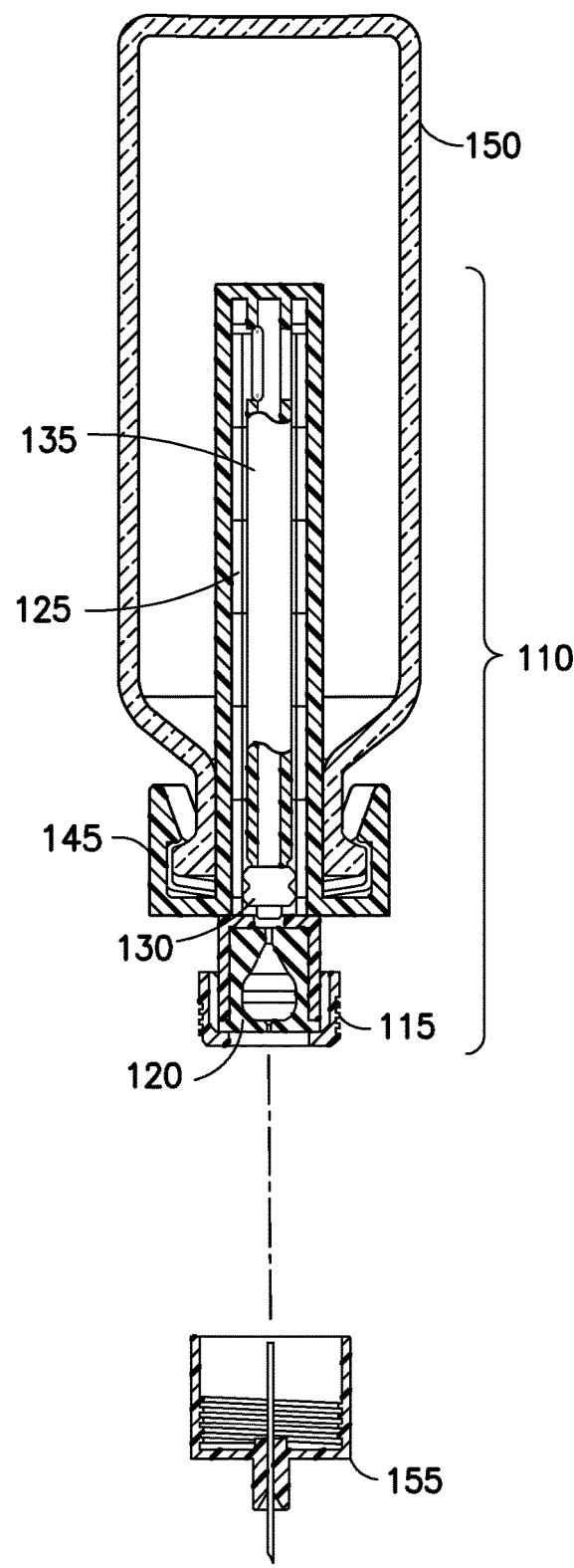
Figure 5E:
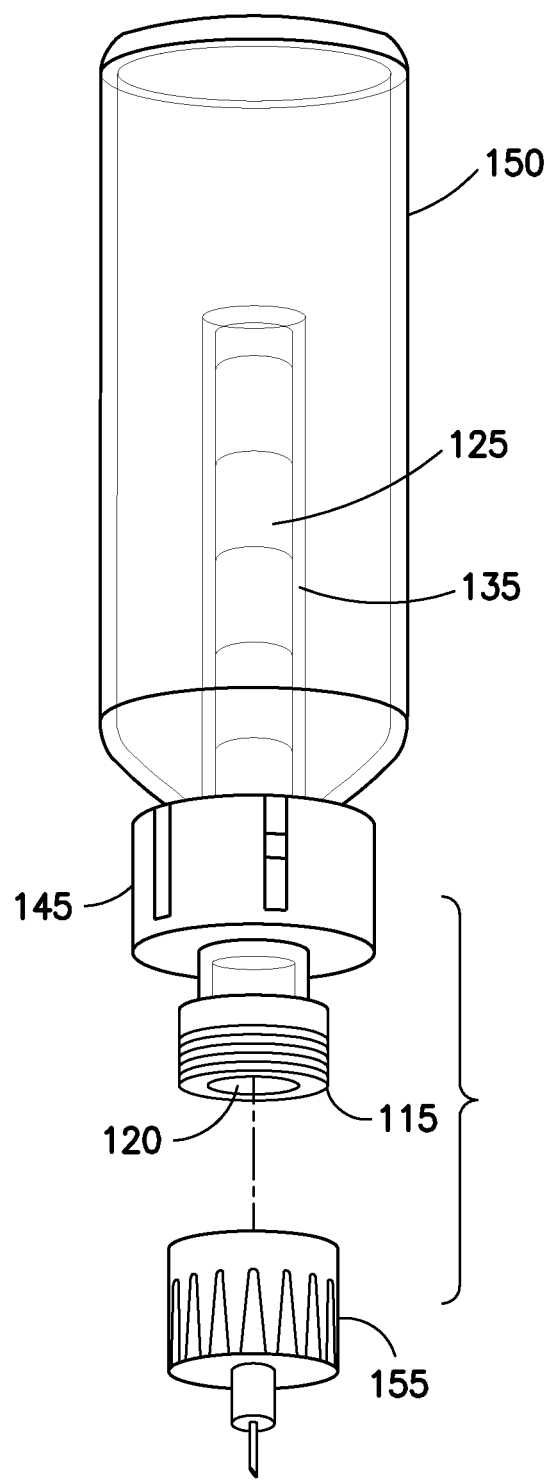
Figure 5F:
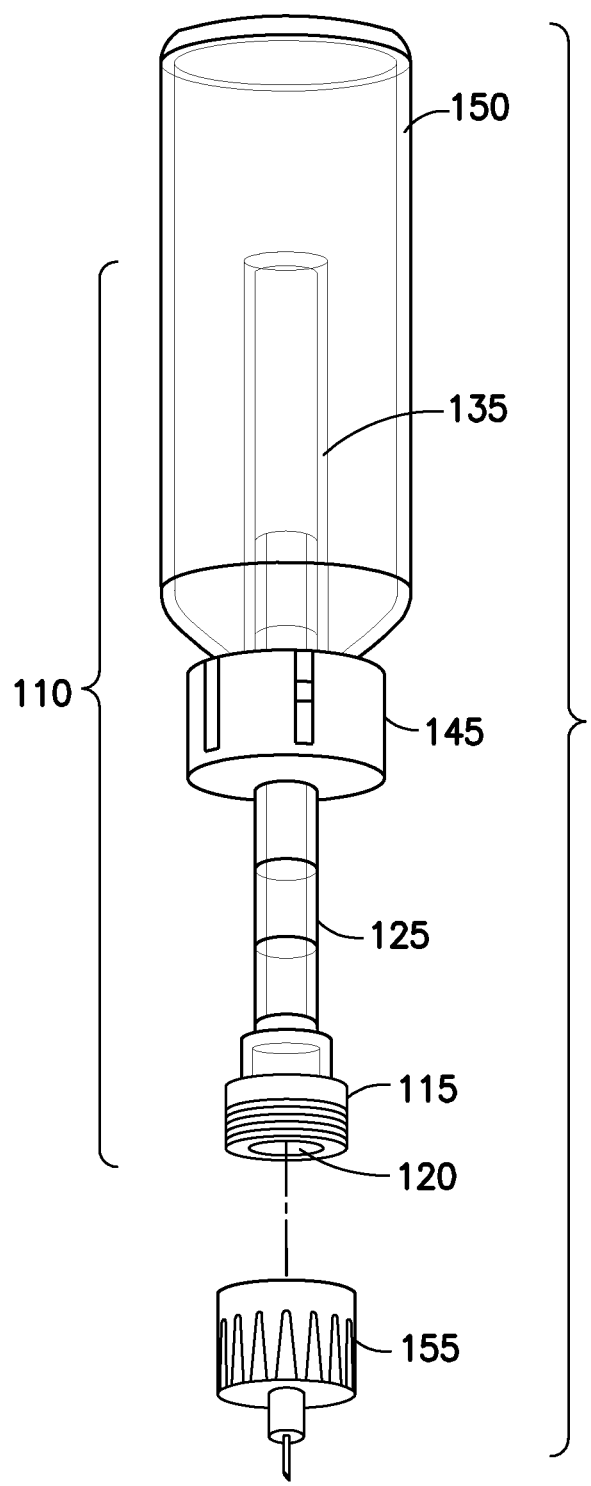

In an illustrative embodiment of the present invention, the vial dosing device 110 is initially packaged in a collapsed configuration, as illustrated in FIGS. 5A, 5D and 5E. In these figures, the plunger tip check valve 130 is disposed adjacent or near the distal end of the dose chamber 125. The plunger tip check valve 130 can rest adjacent to the dose chamber septum 120, and a majority of the plunger 135 can be disposed within the dose chamber 125.

In operation, the user pulls the dose chamber 125 to displace it distally with respect to the cannulated plunger 135 (i.e., away from a vial 150) to draw an appropriate dose of medicament from the vial 150. The user can withdraw a desired dose of medicament by reading dose measurements represented by scale markings on side walls of the dose chamber 125.

In operation, prior to injecting the withdrawn medicament into a layer of tissue or other injection site, the user couples a needle 155 to the submerged vial dosing device 110, for example, by threading or otherwise coupling the needle 155 onto the needle adapter 115 of the vial dosing device 110. The needle 155 can be, for example, a double-ended pen needle, and when coupled the proximal end of the needle 155 pierces the dose chamber septum 120, creating a fluid path for fluid flow from the dose chamber 125, through the needle 155.

The user primes the submerged vial dosing device 110 by holding the vial 150 and the connected submerged vial dosing device 110, with the vial 150 preferably oriented upward. Then, the user displaces the dose chamber 125 proximally with respect to the cannulated plunger 135 to eject any excess air or adjust the dose of medicament prior to injecting the medicament.

The user injects the withdrawn medicament by piercing a layer of tissue or other injection site with the distal end of the needle 155 and then pressing the vial 150 and plunger 135 distally with respect to the dose chamber 125 and toward the layer of tissue or other injection site to expel the dose of medicament from the dosing chamber 125, through the needle 155, and into the layer of tissue or other injection site.

The submerged vial dosing device 110 can remain coupled to the vial 150 for repeated injections until the medicament within the vial 150 is exhausted.

Although not illustrated, a venting check valve like venting check valve 40, for example, in FIG. 2B, can be coupled to the connecting body 145, to adapt the connecting body 145 for air flow from outside the vial 150 through the venting check valve, through at least a portion of the connecting body 145, and into the vial 150. The venting check valve can include any check valve known in the art, including, but not limited to, a press-in check valve. In operation, when the user pulls the dose chamber 125 to displace it distally with respect to the cannulated plunger 135 (i.e. away from the vial 150), air is drawn into the vial 150 through the venting check valve and a vacuum can be created in the dose chamber 125 that pulls medicament from the vial through the plunger tip check valve 130, and into the dose chamber 125.

Although only a few illustrative embodiments of the present invention have been described in detail above, those skilled in the art will readily appreciate that many modifications are possible in the illustrative embodiments without materially departing from the novel teachings and advantages of this invention. Accordingly, all such modifications are intended to be included within the scope of this invention.

The invention claimed is:

1. A vial dosing device, comprising:
    a connecting body coupleable to a vial;
    a hollow plunger adapted for fluid flow therethrough, the hollow plunger being coupled to the connecting body;
    a dose chamber adapted to slidably receive a distal end of the hollow plunger and to expel medicament through a distal end of the dose chamber; and
    a plunger tip check valve coupled to the hollow plunger, and adapted for fluid flow from the hollow plunger through the plunger tip check valve into the dose chamber;
    wherein a majority of the hollow plunger is disposed in the vial when the connecting body is coupled to the vial.

2. The vial dosing device of claim 1, wherein medicament flows from the hollow plunger, through the plunger tip check valve, and into the dose chamber when the dose chamber is displaced distally with respect to the hollow plunger.

3. The vial dosing device of claim 1, wherein in a collapsed configuration:
    the plunger tip check valve is disposed adjacent to a distal end of the dose chamber; and
    a majority of the hollow plunger is disposed within the dose chamber.

4. The vial dosing device of claim 1, wherein the connecting body is a snap-connect body.

5. The vial dosing device of claim 1, wherein the plunger tip check valve is a low durometer check valve.

6. The vial dosing device of claim 1, wherein the plunger tip check valve is a duck-bill shaped check valve.

7. The vial dosing device of claim 1, further comprising:
    a dose chamber septum disposed within the dose chamber at a distal end thereof; and
    a needle adapter coupled to the dose chamber.

8. The vial dosing device of claim 7, wherein the needle adapter is couplable to a pen needle.

9. A combination, comprising:
    the vial dosing device of claim 8; and
    a pen needle coupled to the needle adapter, a proximal end of the pen needle piercing the dose chamber septum.

10. The combination of claim 9, wherein medicament flows from the dose chamber through the pen needle.

11. The vial dosing device of claim 1, further comprising a venting check valve coupled to the connecting body, and adapted for air flow through at least a portion of the connecting body.

12. The vial dosing device of claim 11, wherein the venting check valve is a press-in check valve.

13. The vial dosing device of claim 11, further comprising a pump adapted for pumping air through the venting check valve.

14. The vial dosing device of claim 13, wherein the pump is couplable to the vial.

15. The vial dosing device of claim 13, wherein the pump comprises:
    a bladder;
    a channel coupled to the bladder and adapted for air flow from the bladder through the channel; and
    a pump check valve coupled to the channel and adapted for air flow from the channel through the pump check valve.

16. The vial dosing device of claim 15, wherein the bladder is substantially resilient.

17. The vial dosing device of claim 15, further comprising an open cell foam inside the bladder to provide resiliency to the bladder.

18. The vial dosing device of claim 15, wherein the pump check valve is a molded duck-bill check valve.

19. The vial dosing device of claim 18, wherein the molded duck-bill check valve comprises polyurethane.

20. The vial dosing device of claim 15, wherein the pump check valve is coupled to the venting check valve and is adapted for air flow through the pump check valve and the venting check valve.

21. A combination, comprising:
the vial dosing device of claim 1; and
a medical vial.

22. The combination of claim 21, wherein the connecting body is coupled to the medical vial.

23. The combination of claim 21, wherein:
the vial dosing device further comprises a venting check valve coupled to the connecting body; and
the venting check valve is adapted for air flow through at least a portion of the connecting body and into the medical vial.

24. The vial dosing device of claim 1, wherein:
the hollow plunger is substantially enclosed by the connecting body; and
the connecting body is at least partially enclosed by the vial.

25. A method of using a vial dosing device, comprising:
coupling a connecting body to a medical vial containing medicament; and
displacing a hollow plunger proximally with respect to a dose chamber, the hollow plunger being coupled to the connecting body, a majority of the plunger being submerged in the medical vial, a distal end of the hollow plunger being slidably received in the dose chamber, to withdraw a dose of medicament from the medical vial into the dose chamber through the hollow plunger and a plunger tip check valve coupled to the hollow plunger.

26. The method of using a vial dosing device of claim 25, further comprising displacing the hollow plunger distally with respect to the dosing chamber to expel medicament from a distal end of the vial dosing device.

27. The vial dosing device of claim 1, wherein the hollow plunger is fixed relative to the vial when the connecting body is coupled to the vial.

28. The vial dosing device of claim 15, wherein the hollow plunger is fixed relative to the vial when the connecting body is coupled to the vial.

\* \* \* \* \*